US012268661B2

(12) United States Patent
MacAllister et al.

(10) Patent No.: US 12,268,661 B2
(45) Date of Patent: Apr. 8, 2025

(54) METHODS OF TREATING ASCITES

(71) Applicant: Martin Pharmaceuticals, Inc., New York, NY (US)

(72) Inventors: Thomas W MacAllister, Arlington, VA (US); Sven M. Jacobson, New York, NY (US)

(73) Assignee: Martin Pharmaceuticals, Inc., New York, NY (US)

( * ) Notice: Subject to any disclaimer, the term of this patent is extended or adjusted under 35 U.S.C. 154(b) by 43 days.

(21) Appl. No.: 17/375,087

(22) Filed: Jul. 14, 2021

(65) Prior Publication Data
US 2021/0338627 A1   Nov. 4, 2021

Related U.S. Application Data

(63) Continuation of application No. 17/090,530, filed on Nov. 5, 2020, now abandoned.

(60) Provisional application No. 63/067,411, filed on Aug. 19, 2020, provisional application No. 62/943,605, filed on Dec. 4, 2019, provisional application No. 62/936,270, filed on Nov. 15, 2019.

(51) Int. Cl.
  *A61K 31/265*   (2006.01)
  *A61K 31/341*   (2006.01)
  *A61K 31/585*   (2006.01)
  *A61P 7/10*   (2006.01)

(52) U.S. Cl.
  CPC .......... *A61K 31/265* (2013.01); *A61K 31/341* (2013.01); *A61K 31/585* (2013.01); *A61P 7/10* (2018.01)

(58) Field of Classification Search
  None
  See application file for complete search history.

(56) References Cited

PUBLICATIONS

Pedersen et al. "Management of Cirrhotic Ascites". Therapeutic Advances in Chronic Disease. 2015; 6(3):124-137. (Year: 2015).*
Rosoff et al. "Studies of Renin and Aldosterone in Cirrhotic Patients with Ascites". Gastroenterology. 1975; 69:698-705. (Year: 1975).*
Siqueira et al. "Refractory Ascites: Pathogenesis, Clinical Impact, and Management". Gastroenterology & Hepatology. 2009; 5(9): 647-656. (Year: 2009).*
Ratain et al. "Principles of Pharmacokinetics". Eds. Kufe DW, Pollock RE, Weichselbaum RR, et al. Holland-Frei Cancer Medicine. Sixth Edition. Hamilton (ON): BC Decker; 2003. pp. 1-8. (Year: 2003).*
Hospira. Dopamine Hydrochloride and 5% Dextrose Injection, USP. Prescribing Information. 2014, p. 1-8. (Year: 2014).*
Lin et al. "Low-Dose Dopamine Infusion in Cirrhosis with Refractory Ascites". Int J Clin Pract. Nov.-Dec. 1998 52(8):533-536. (Abstract Only) (Year: 1998).*
Tsunoda et al. "Treatment for Ovarian Hyperstimulation Syndrome Using an Oral Dopamine Prodrug, Docarpamine". Gynecol Endocrinol. Aug. 2003; 17(4):281-286. (Abstract Only) (Year: 2003).*
Lin SM, Lee CS, Kao PF. Low-dose dopamine infusion in cirrhosis with refractory ascites. Int J Clin Pract. Nov.-Dec. 1998 52(8):533-6.
Hadengue A, et al. Hepatology. Jan. 1991; 13(1):111-6.
Yannick Bacq et al. Systemic, splanchnic and renal hemodynamic effects of a dopaminergic dose of dopamine in patients with cirrhosis. Hepatology. 1991. 14(3): 483-487.
Barnardo De et al. Effects of Dopamine on Renal Function in Patients with Cirrhosis. Gastroenterology. 1970. 58(4): 524-531.
Mostbecka et al. The simultaneous investigation of liver and kidney function in the presence of dopamine. Wien Klin Wochenschr. Oct. 17, 1975;87(19):639-42.
Carmelita R. EspirituJose P. Mendoza, Billy K. Yeh. Effects of Intravenous Infusion of Dopamine in Cirrhotics. Proc Soc Exp Biol Med. Oct. 1972;141(1):331-5.
Runyon BA, et al. Annals. of Internal Medicine. 1992; 117:215-220.
Salerno F et al. Refractory ascites: pathogenesis, definition and therapy of a severe complication in patients with cirrhosis. Liver Int. 2010; 30(7):937-947.
P Gines, et al. Compensated cirrhosis: natural history and prognostic factors. Hepatology. Jan.-Feb. 1987;7(1):122-8.
Piano S, Tonon M, Angeli P. Management of ascites and hepatorenal syndrome. Hepatol. Int. 2018; 12(Suppl 1):122-134.
Zhao R, Lu J, Shi Y, et al. Current management of refractory ascites in patients with cirrhosis. J. Int. Med. Res. 2018; 46(3):1138-1145.
Funasaki T, et al. Effects of a new orally active dopamine prodrug, docarpamine, on refractory ascites: A pilot study. Am. J. Gastroenterology. 1999; 94(9):2475 2481.
Arroyo V et al. Definition and diagnostic criteria of refractory ascites and hepatorenal syndrome in cirrhosis. International Ascites Club. Hepatology. Jan. 1996;23(1): 164-76.

(Continued)

*Primary Examiner* — Leslie A. Royds Draper
(74) *Attorney, Agent, or Firm* — Thomas W. MacAllister

(57) ABSTRACT

The invention relates to the treatment of ascites, and especially refractory ascites, with an orally bioavailable prodrug of dopamine. A preferred prodrug of dopamine is docarpamine. In one embodiment treated patients are, prior to treatment, on doses of furosemide >80 mg/day and/or spironolactone >100 mg/day or equivalent doses of an alternative loop-acting and/or distal-acting diuretic. The ascites treated by the invention are typically caused by liver cirrhosis due to alcohol or non-alcoholic fatty liver disease and generally not due to viral hepatitis or primary biliary cholangitis. Typical patients have an activated renin-angiotensin-aldosterone levels as may be indicated by elevated levels of renin and/or aldosterone. Refractory ascites treatable according to the invention are such that patients beginning treatment require large volume paracentesis at a minimum of: (a) 3 times in 60 days, (b) 4 times in 90 days or (c) at least once every 30 days over a 90-day period. The invention also contemplates treating diuretic intractable ascites. Target plasma dopamine levels are disclosed by with dosing with the contemplated dopamine prodrugs may be guided. Preferred dosing is greater that 2250 mg per day, with more preferred doses exceeding 3500 mg per day.

12 Claims, No Drawings

(56) References Cited

PUBLICATIONS

Moore KP et al. The management of ascites in cirrhosis: report on the consensus conference of the International Ascites Club. Hepatology. Jul. 2003;38(1):258-66.

* cited by examiner

METHODS OF TREATING ASCITES

CROSS REFERENCE TO RELATED APPLICATIONS

This application is a continuation of U.S. application Ser. No. 17/090,530, which claims priority from U.S. provisional Ser. No. 62/936,270, filed 15 Nov. 2019, U.S. provisional Ser. No. 62/943,605, filed 4 Dec. 2019 and U.S. provisional Ser. No. 63/067,411, filed 19 Aug. 2020.

BACKGROUND OF THE INVENTION

Ascites is a pathologic accumulation of fluid within the peritoneal cavity. It is most commonly associated with cirrhosis of the liver (84% of cases), but is also seen with some forms of cancer (6% of cases, most frequently associated with breast, bronchus, ovary, stomach, pancreas and colon cancer), heart failure (3%), tuberculosis (1%), dialysis, pancreatic disease and other conditions (Runyon 1992).

Refractory Ascites (RA) is a serious medical complication of liver cirrhosis that occurs when ascites can no longer be treated with diuretics and salt restriction, and requires additional and repeated clinical intervention, including large volume paracentesis. It is associated with a significant shortening of life expectancy, increased use of medical resources, and ultimately is only curable by liver transplantation.

The pathophysiology underlying cirrhotic ascites is related to a combination of two pathogenetic mechanisms: portal hypertension and renal sodium retention as a consequence of arterial underfilling. An increased resistance to portal flow at the sinusoidal level leads to the development of sinusoidal portal hypertension and the backward transmission of this increased pressure into splanchnic capillaries. The result is that the excess of fluid preferentially localizes in the peritoneal cavity. A decrease in effective arterial blood volume due to vasodilator factors such as nitric oxide leads to the activation of anti-natriuretic and vasoconstrictor factors (mainly renin-angiotensin—aldosterone system, sympathetic nervous system and arginine vasopressin) with subsequent sodium retention. The main consequence of these hemodynamic and renal alterations is a continuous escape of fluid from the hepatic sinusoids and from the splanchnic capillaries into the interstitial space. This spillover is initially compensated by an increased return of fluids to the systemic circulation through the lymphatic system and the thoracic duct. However, as cirrhosis progresses, the escape of fluids overcomes the lymphatic return, leading to progressive accumulation of fluid directly into the peritoneal cavity. This is followed by a further activation of the renal mechanisms of sodium and water re-absorption that is crucial to perpetuate ascites formation (Salerno 2010, Pose 2017).

Within 10 years after the diagnosis of compensated cirrhosis, about 50 percent of patients will have developed ascites (Gines 1987). Ascites is normally treated with a combination of diuretics (with spironolactone and furosemide most commonly used) and restricted salt intake. With this regimen ascites can be managed in the majority of patients. Patients with cirrhosis and a first onset of ascites have a probability of survival of 85% during the first year and 56% at 5 years without liver transplantation (Pose 2017).

Ascites deteriorates to RA via the following pathophysiological mechanism. The severity of renal sodium retention increases throughout the natural history of cirrhosis, because of the progression of systemic and portal hemodynamic abnormalities and the associated activation of neuro-humoral vasoactive systems leading to avid renal reabsorption of sodium and water. At the same time, renal perfusion and glomerular filtration rate progressively decline. As a result, sodium re-absorption at the proximal convoluted tubule markedly increases and its delivery to distal segments of the nephron is markedly reduced. Thus, renal sodium retention mainly occurs proximally to the site of action of both anti-mineralocorticoid and loop diuretics (e.g. spironolactone and furosemide), and this can explain why diuretic treatment becomes unsuccessful in some patients. In addition, the reduced cardiovascular responsiveness to vasoconstriction perpetuates the relative under-filling of the effective arterial blood volume and this compounds the hypovolemic effects of diuretics (Salerno 2010). Iatrogenic factors may also contribute. These include the administration of non-steroidal anti-inflammatory drugs which impair renal function by inhibiting the synthesis of vasodilating prostaglandins, the administration of angiotensin-I-converting enzyme inhibitors or angiotensin receptor antagonists, which can impair the renal blood perfusion and reduce the glomerular filtration rate (GFR) or the administration of nephrotoxic drugs such as aminoglycosides. Finally, complications including fluid loss through vomiting, diarrhea or bleeding, or bacterial infections such as spontaneous bacterial peritonitis, can intensify arterial vasodilatation and worsen the mismatch between the intravascular volume and the vascular capacitance (Salerno 2010).

At present, the only curative intervention for RA is liver transplantation, but this option is not available for many patients for a variety of reasons including general medical condition and absence of suitable donor organs. Treatment options available to patients with RA include repeated large volume paracentesis (LVP), transjugular intrahepatic portosystemic shunt placement (TIPS), experimental automated low-flow pumps and the administration of vasoconstrictors (Piano 2018).

Paracentesis, the oldest treatment of ascites, is still the first-line treatment for RA. LVP is effective especially in patients with tense (grade 3) ascites. Large-volume paracentesis (>5 L of ascites removed) combined with albumin i.v. infusion (6-8 g/L of ascites removed) and saline as plasma expanders to prevent paracentesis induced circulatory dysfunction, is more effective than diuretics and causes fewer complications (La Mura 2016, Pose 2017). It shortens hospital stay but it has no effect on mortality rate (Zhao 2018). The procedure should be avoided in patients with disseminated intravascular coagulation, and should be performed with caution in patients with intra-abdominal adhesions or with a distended urinary bladder (Salerno 2010). Paracentesis is invasive and subjects a fragile population to the repeated risk of infection, an important factor the transformation of a relatively stable condition into acute decompensation and even acute-on-chronic liver failure that has a 90-day mortality rate that can range upwards of 75-80%.

The use of vasoconstrictor drugs can improve the underlying hemodynamic derangements that lead to ascites formation in cirrhosis, thereby reducing the activity of antinatriuretic factors. Data are available on the use of vasoconstrictors (midodrine, clonidine, dopamine and terlipressin) with plasma expansion in patients with cirrhosis and ascites. These drugs may improve renal function, urinary sodium excretion, and serum sodium levels in patients with advanced cirrhosis and hepatorenal syndrome (Pose 2017).

Dopamine produces natriuretic and positive inotropic effects when administered intravenously, but it is not bioavailable when administered orally due to high rates of metabolism in the gut and the liver. The dopamine prodrug docarpamine has been reported to be effective in a small cohort of RA patients (Funasaki 1999). None of the vasoconstrictor drugs have been approved for the treatment of ascites or RA in the U.S. and many studies on the renal effects of dopamine and related drugs suggest it would not be effective in treating ascites or RA.

Positive effects of dopamine at 2 ug/kg/min on effective renal plasma flow were reported in patients with RA, but with no difference in the changes of blood urea nitrogen, creatinine, creatinine clearance, blood pressure, pulse rate, serum sodium, serum aldosterone and GFR (Lin 1998). Consistently, dopamine at 1.5 ug/kg/min did not enhance GFR (Bacq 1991). Dopamine at 1.3-3 ug/kg/min did not change urine volume, urine sodium or GFR (Barnardo 1970). Dopamine at 200 ug/min did not significantly change GFR. Espiritu 1972 did observe non-significant increases in urine volume and GFR at 2 ug/kg/min. Similarly, the dopamine agonist fenoldopam failed to increase urine volume or urine sodium (Hadengue 1991).

In view of the foregoing, there remains an urgent need for additional treatment options for RA and it is the aim of the present invention to provide new therapeutic approaches for RA.

SUMMARY OF THE INVENTION

In one embodiment, the invention contemplates a method of treating a patient with ascites, comprising administering to said patient a therapeutically effective amount of docarpamine, wherein, prior to said administering, the patient is treated for more than 1 week with doses of furosemide >80 mg/day and/or spironolactone >100 mg/day or equivalent doses of an alternative loop-acting and/or distal-acting diuretic. Further to this aspect of the invention, it is further contemplated that the dose of diuretic agents in the patient is not limited by diuretic-induced renal impairment. In preferred embodiments, the method further contemplates at least one second administration of docarpamine during which said patient is also being treated with furosemide >80 mg/day and/or spironolactone >100 mg/day.

Another embodiment of the invention relates to a method of treating a patient with ascites, comprising administering to said patient a therapeutically effective amount of docarpamine, wherein said ascites is caused by liver cirrhosis due to alcohol or non-alcoholic fatty liver disease.

Still another embodiment relates to a method of treating a patient with ascites, comprising administering to said patient a therapeutically effective amount of docarpamine, wherein said ascites is not caused by cirrhosis due to viral hepatitis or primary biliary cholangitis.

Yet another embodiment contemplates a method of treating a patient with ascites, comprising administering to said patient a therapeutically effective amount of docarpamine, wherein said patient has a serum aldosterone level exceeding 21 ng/dL (582.5 pmol/L) and or a serum renin concentration exceeding 40 pg/mL (1.0 pmol/L).

A further embodiment of the invention envisions a method of treating a patient with ascites, comprising administering to said patient a therapeutically effective amount of docarpamine, wherein, prior to treatment, said patient required large volume paracentesis at a minimum of: (a) 3 times in 60 days, (b) 4 times in 90 days or (c) at least once every 30 days over a 90-day period.

Another embodiment of the invention involves a method of treating a patient with diuretic intractable ascites, comprising administering to said patient a therapeutically effective amount of docarpamine, wherein said a patient experienced one or more diuretic-induced complications selected from the group consisting of: diuretic-induced hepatic encephalopathy; diuretic-induced renal impairment; diuretic-induced hyponatremia; and diuretic-induced hypokalemia.

Yet another embodiment contemplates a method of treating a patient with ascites, comprising administering to said patient a therapeutically effective amount of docarpamine, wherein said patient is unresponsive to sodium-restricted diet and intensive diuretic therapy.

Yet another embodiment relates to a method of treating a patient with ascites, comprising: administering to said patient a first amount of docarpamine; obtaining the concentration of dopamine in the blood, serum or plasma of said patient; and administering a second amount of docarpamine to said patient, wherein said second amount is selected based on the concentration of dopamine obtained. Such an embodiment is particularly useful in a Caucasian or non-Asian populations and any other population in which the metabolic profile of docarpamine is highly variable.

A particularly preferred embodiment relates to a method of treating a patient with ascites, comprising administering to said patient a total daily dose of 4500 mg of docarpamine, administered 2-3 times per day to achieve the total daily dose. Pre-treatment, ascites patients are preferably receiving regular large volume paracentesis.

DETAILED DESCRIPTION OF THE INVENTION

The present invention relates to the treatment of a patient with ascites. Ascites is commonly called excess abdominal fluid or abnormal accumulation of fluid in the abdominal cavity. Many underlying diseases can be responsible for causing ascites, including tuberculosis, kidney disease, pancreatitis, and an underactive thyroid. Ascites may develop in cancer when it affects the peritoneum, liver, lymphatic system, ovaries, breast, colon, stomach, pancreas, lung, or cervix. The primary causes of ascites are heart failure, cirrhosis (cirrhotic ascites), and cancer (malignant ascites), with cirrhosis being responsible for more than 80% of ascites cases.

In contrast to cirrhotic and other forms of ascites, malignant ascites (MA) occurs via a combination of altered vascular permeability and obstructed lymphatic drainage (Hodge and Badgwell, 2019). In MA, tumor cells lining the peritoneum secrete protein-rich fluid and extracellular enters the peritoneal cavity to maintain oncotic balance (Frick and Schölmerich, 2005). Cancers express factors that mediate increased capillary permeability, facilitating this fluid movement (Hodge and Badgwell 2019). A significant difference in MA relative to other ascites is that tumor cells in the peritoneal cavity directly obstruct lymphatic channels, leading to impaired uptake of fluid into the lymphatic system (Hodge and Badgwell 2019). Unlike other ascites etiologies, there is no antidiuretic effect at issue indicating that diuretics should be ineffective, which they are, and that dopamine and, therefore dopamine prodrugs like docarpamine should likewise be ineffective.

Accordingly, patients treatable using the invention may, for example, have heart failure or cirrhosis or ascites due to other causes like tuberculosis, dialysis (nephrogenous), biliary dysfunction and fulminant hepatic failure, MA is excluded from the invention. Treatable patients preferably have cirrhosis of the liver as the cause underlying the ascites.

Ascites in hepatocellular carcinoma is considered to be due to the underlying cirrhosis, and not due to mechanisms associated with MA and so treating patients with ascites due to hepatocellular carcinoma is included in the invention since they are not understood to have MA.

Preferred embodiments of the invention pertain to treating cirrhotic ascites. More preferred embodiments of the invention involve treating a patient with ascites, irrespective of cause, who is not effectively managed such that the patient undergoes frequent large volume paracentesis.

Preferred causes of cirrhotic ascites contemplated by the invention result from cirrhosis due to alcohol and cirrhosis due to non-alcoholic fatty liver disease. Certain embodiment of the invention are understood to exclude ascites resulting from cirrhosis caused by viral hepatitis, such as hepatitis b or hepatitis c. Other embodiments exclude ascites resulting from cirrhosis caused by primary biliary cholangitis.

"Effectively managed," when referring to the ascites patient generally means the patient has been instructed to restrict sodium intake and management using diuretic has proved effective. In such a patient where diuretic treatment proves to be ineffective, the patient is not considered to be effectively managed. Diuretic treatment is ineffective either because the patient is diuretic resistant or diuretic intractable. A diuretic resistant patient does not respond to effective doses of diuretics. A diuretic intractable patient cannot be effectively treated with diuretics due to some safety or tolerability issue that limits the dose or the ability to use diuretics altogether.

Paracentesis is a procedure by which ascitic fluid is removed from the abdomen using a needle or catheter. Paracentesis may be performed for diagnostic purposes, but in the present case it is done for therapeutic purposes to remove fluid and alleviate the pressure created by the large volume of fluid, which distends the abdomen and compresses internal organs. Large volume paracentesis (LVP) generally involves the removal of 5 liters or more of ascitic fluid from the abdomen. In some instances, it can involve the removal of 2, 3, 4, or 6, 7, 8, 9, 10 or more liters of ascitic fluid from the abdomen. The word "frequent" when used with LVP generally refers to at least one LVP at least every two months and generally at least every six weeks. More preferably, frequent LVP entails LVP at least once a month. In some cases, frequent LVP patients treated according to the invention have LVP every 3, 2 or even 1 week in certain cases. "Frequent" specifically contemplates LVP at a minimum of: (a) 3 times in 60 days, (b) 4 times in 90 days or (c) at least once every 30 days over a 90-day period.

The treatment of a patient undergoing frequent LVP according to the invention refers to the patient at baseline, before treatment is started. Once treatment according to the invention is started, the frequency of LVP and/or the volume of ascites will decrease over time and so any treatment after the initial treatment is still considered to be a treatment of a patient undergoing frequent LVP because that was the patient's condition at baseline.

Docarpamine is an orally-active prodrug of dopamine; dopamine is not orally bioavailable due to rapid metabolism in the small intestine and liver after administration (Merits 1973). Dopamine is a sympathomimetic amine vasopressor that is the naturally occurring immediate precursor of norepinephrine. Dopamine produces natriuretic and positive inotropic effects when administered intravenously. It is indicated for the correction of hemodynamic imbalances present in the shock syndrome due to myocardial infarction, trauma, endotoxic septicemia, open-heart surgery, renal failure, and chronic cardiac decompensation as in congestive failure. Its use is approved when there is poor perfusion of vital organs, low cardiac output and/or hypotension (FDA, dopamine label).

Docarpamine is not approved in the US, but it has been available in Japan since 1995 under the brand name Tanadopa by Mitsubishi Tanabe Pharmaceutical Company. The drug is used to wean patients with circulatory failure off of intravenous dopamine. Docarpamine is rapidly metabolized to free dopamine in the small intestine and liver and results in the detection of elevated circulating dopamine levels. The structure of docarpamine is provided below.

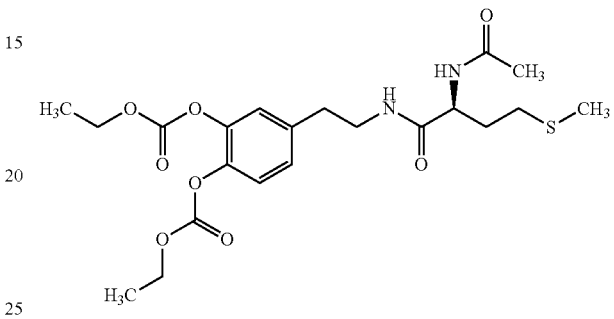

At low rates of infusion (0.5-2 mcg/kg/min) dopamine causes vasodilation that is presumed to be due to a specific agonist action on dopamine receptors (distinct from alpha- and beta-adrenoceptors) in the renal, mesenteric, coronary, and intracerebral vascular beds. The vasodilation in these vascular beds is accompanied by increased glomerular filtration rate, renal blood flow, sodium excretion, and urine flow. Hypotension sometimes occurs.

At intermediate rates of infusion (2-10 mcg/kg/min) dopamine acts to stimulate the beta1 adrenoceptors, resulting in improved myocardial contractility, increased sino-atrial rate and enhanced impulse conduction in the heart. There is little, if any, stimulation of the beta2-adrenoceptors (peripheral vasodilation). Dopamine causes less increase in myocardial oxygen consumption than isoproterenol, and its use is not usually associated with a tachyarrhythmia. Clinical studies indicate that it usually increases systolic and pulse pressure with either no effect or a slight increase in diastolic pressure. Blood flow to the peripheral vascular beds may decrease while mesenteric flow increases due to increased cardiac output. Total peripheral resistance (alpha effects) at low and intermediate doses is usually unchanged.

At higher rates of infusion (10-20 mcg/kg/min) there is some effect on alpha-adrenoceptors, with consequent vasoconstrictor effects and a rise in blood pressure. The vasoconstrictor effects are first seen in the skeletal muscle vascular beds, but with increasing doses, they are also evident in the renal and mesenteric vessels. At very high rates of infusion (above 20 mcg/kg/min), stimulation of alpha-adrenoceptors predominates and vasoconstriction may compromise the circulation of the limbs and override the dopaminergic effects of dopamine, reversing renal dilation and natriuresis.

In practicing the inventive methods, docarpamine is generally administered in order to target engagement of the renal dopamine receptors, responsible for increased glomerular bloodlfow and diuresis. Increases in cardiac output mediated by beta 1 adrenergic receptors may also be beneficial in terms of increasing renal perfusion and so the inventive methods contemplate dosing that may increase cardiac output. Generally, doses of docarpamine will avoid clinically observable (by increases in blood pressure) systemic alpha adrenergic effects, though subclinical effects are contemplated and may be beneficial. Accordingly, usually the inventive methods use doses that do not materially alter the blood pressure of the patient. The maximum target plasma levels of free dopamine will generally not exceed those obtained with a dopamine infusion of about 10-15 mcg/kg/min. More typically, such target plasma levels will not exceed those obtained with a dopamine infusion of about 10 mcg/kg/min. In preferred embodiments, target plasma levels will be in the range of those obtained with a dopamine infusion of about 2 to about 7 mcg/kg/min and most preferably from about 2 to about 5 mcg/kg/min.

Some of the inventive methods involve treating a patient with at least one dose of docarpamine, measuring the amount of free dopamine in the blood and then administering at least one additional dose of docarpamine that is determined based on maintaining dopamine plasma levels within the foregoing target plasma levels. Typical target plasma levels for dopamine will be between 1 and 300 ng/ml. Preferable target plasma levels will be between 10 and 150 ng/ml with more preferred target plasma levels being from 20-110 ng/ml or 20-80 ng/ml. Most preferred target plasma levels are from 40-80 ng/ml.

Typical daily doses of docarpamine will not exceed 6,750 mg per day and generally will be between 750 mg and 5000 mg per day. While a total daily dose of 2250 mg is contemplated, higher doses of between more than 2250 mg, but less than 6750 mg are preferred. On preferred range is 2250-6750 or 3000 to 6750 mg, with the range 3500 mg to 5500 mg being contemplated within that range, 4500 mg per day is particularly preferred, with ranges around that being 4000 mg to 5000 mg. The total daily dose is generally administered in more than one daily dose and usually 2-3 doses of equal amount per day comprise the total daily dose. Dosing preferably continues for more than 7 days and typically continues for at least one month. More preferably dosing continues for at least 3 months or at least 6 months.

The invention further contemplates the use of other oral prodrugs of dopamine, which upon administration to the body are converted to dopamine. An example of such oral prodrug of dopamine is 1-DOPA, also known as levodopa or 1-3,4-dihydroxyphenylalanine. Unlike docarpamine, levodopa is not derivatized at the catechol moiety (the two —OH groups on the aromatic ring), but is derivatized as a simple peptide bond at the amino group. The structure of levodopa is compared to dopamine is as follows:

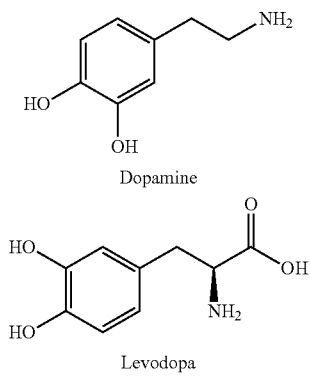

Generally, orally bioavailable prodrugs will be derivatized similarly to docarpamine and levodopa to product the amino group (preferably by forming a peptide bond) and/or one or both of the hydroxyl groups of the catechol moiety, generally as an ester. One skilled in the art will readily understand the types of modifications that can be made to dopamine in order to create additional dopamine prodrugs. Dosing of such additional prodrugs may be guided by the same principles set out above relating to target plasma dopamine concentrations using methods well known to those skilled in the art. Dosing for levodopa in order to achieve such plasma dopamine concentrations will generally require at least 1 gram per day and not more than 5 grams per day and preferably from 2, 3 or 4 grams per day, most preferably 2-3 grams per day.

Grading Ascites

The methods of the invention involve treating patients with ascites, which are graded according to the following criteria:

Grade 1 ascites is mild and can be detected only by an examination such as ultrasound;

Grade 2 ascites is moderate and evidenced by moderate distension of the abdomen, and is therefore readily detectable on physical examination; and Grade 3 ascites is large with marked distension of the abdomen.

The inventive methods are particularly adapted to treating higher grades of ascites, most particularly Grade 3 and sometimes Grade 2.

Refractory Ascites

The inventive methods are useful in the treatment of refractory ascites. There are a number of definitions of Refractory Ascites and the treatment of patients that fall under one or more of these definitions is hereby contemplated. Exemplary definitions have been provided by the American Association for the Study of Liver Disease (AASLD), the European Association for the Study of the Liver (EASL), the International Club for Ascites (ICA) and the Asia Pacific Association for the Study of the Liver (APASL).

As generally referred to herein, refractory ascites is defined as ascites that does not resolve or that recurs shortly after therapeutic paracentesis, despite sodium restriction and diuretic treatment (Siqueira 2009). Refractory ascites includes two subgroups (EASL 2010): diuretic-resistant ascites and diuretic intractable ascites. Diuretic-resistant patients are those who fail to respond to intensive treatment with diuretics. Diuretic-intractable patients are those who could not tolerate an effective dose of diuretic.

Sodium restriction is the universally accepted first step in trying the manage ascites. Instructions are provided to patients regarding managing sodium intake, but this cannot be reasonably monitored by the physician in an outpatient population. Accordingly, while patients are instructed in this regard, enforcement of sodium restriction is not a requirement for regarding a patient as refractory; it is sufficient that instructions are given.

Widely considered the seminal work in refractory ascites and used as the foundational definition for most others, including EASL, Arroyo (1996) defines refractory ascites as ascites that cannot be mobilized or the early recurrence of which (i.e., after therapeutic paracentesis) cannot be satisfactorily prevented by medical therapy. Refractory ascites includes both diuretic-resistant ascites and diuretic intractable ascites. Diuretic-resistant ascites are ascites that cannot be mobilized or the early occurrence of which cannot be prevented because of lack of response to dietary sodium restriction and intensive diuretic treatment. Diuretic-intractable ascites are ascites that cannot be mobilized or the early occurrence of which cannot be prevented because of the development of diuretic-induced complications that preclude the use of an effective diuretic dosage.

According to the criteria of the International Ascites Club, refractory. ascites is defined as "ascites that cannot be mobilized or the early recurrence of which (i.e., after LVP) cannot be satisfactorily prevented by medical therapy"

Consistent with Arroyo (1996), the following criteria were adopted by the International Club of Ascites in defining diuretic resistant ascites (Moore 2003) and they are adopted for the purposes of the present invention:
1. "Intensive diuretic therapy" means spironolactone at 400 mg/day and furosemide at 160 mg/day for at least 1 week with a salt-restricted diet (<5.2 g of salt/day);
2. "Lack of response" is defined as a mean weight loss of <0.8 kg over 4 days and a urinary sodium output less than the sodium intake;
3. "Early recurrence" is defined as the reappearance of grade 2 or 3 ascites within 4 weeks of initial mobilization; and
4. "Diuretic-induced complications" include, diuretic-induced hepatic encephalopathy, diuretic-induced renal impairment, diuretic-induced hyponatremia, and diuretic-induced hypokalaemia.

Diuretic-induced hepatic encephalopathy is defined as development of encephalopathy without any other precipitating factor. Diuretic-induced renal impairment is defined as an increase in the serum creatinine level of >100% to a value >2 mg/dL in patients with treatment-responsive ascites. Diuretic-induced hyponatremia is defined as a decrease in the serum sodium level of >10 mmol/L or a serum sodium level of <125 mmol/L. Diuretic-induced hypokalaemia or hyperkalaemia is defined as a change in serum potassium to <3 mmol/L or >6 mmol/L, despite appropriate measures. Each of the foregoing complications may be a factor in eliminating diuretic therapy or reducing diuretic doses to levels at which patients are no longer effectively managed and, therefore, are deemed diuretic intractable, one subtype of refractory ascites.

Accordingly, the treatment of patients with diuretic intractable ascites is specifically contemplated. Specific embodiments of treating a patient with intractable ascites include methods of treating a patient with diuretic intractable ascites, comprising administering to said patient a therapeutically effective amount of docarpamine, wherein said a patient experienced one or more diuretic-induced complications selected from the group consisting of: diuretic-induced hepatic encephalopathy; diuretic-induced renal impairment; diuretic-induced hyponatremia; or diuretic-induced hypokalaemia.

The AASLD defines RA as fluid overload that 1) is unresponsive to sodium-restricted diet and high-dose diuretic treatment (400 mg/day of spironolactone and 160 mg/day of furosemide), or 2) recurs rapidly after therapeutic paracentesis) (Runyon 2013).

One preferred embodiment of the invention relates to treating ascites patients who have been treated with elevated doses of diuretics. Typically, patients will be treated with a combination of a loop diuretic and a distal acting diuretic. Furosemide is a usual example of the loop diuretic and spironolactone is an example of a distal acting diuretic. Such patients will have been treated with doses of furosemide >80 mg/day and/or spironolactone >100 mg/day or equivalent doses of an alternative loop-acting and/or distal-acting diuretic for at least one week preceding treatment with docarpamine in accordance with the invention. Preferred ranges for furosemide are at least >80-100, 100-150, 150-200, 200-250, 250-300, 300-350 and 350-400 mg per day. Preferred doses of spironolactone include >100-110, 110-120, 120-130, 130-140, 140-150 and 150-160 mg/day. In some rare cases, spironolactone may be administered in doses of greater than 160 mg/day, for instance at 300 or even 350 mg per day. Equivalent doses of alternative loop diuretics and distal acting diuretics may be determined by the skilled person and also applied to the inventive methods. In particularly preferred embodiments, at least one dose of docarpamine with be administered while the patient is one such elevated doses of one or more diuretics. In certain of these embodiments, docarpamine will be administered in conjunction with one or more diuretics in accordance with the foregoing dosing ranges. In some cases, patients will not be taking diuretics at the time docarpamine treatment is initiated and diuretics will be titrated to an effective dose while patients are being treated with docarpamine. In such cases, it is often found that patients who do not respond to diuretics or who have stopped responding to diuretics will become responsive to diuretics when on docarpamine therapy.

In other embodiments, patients are also treated with other vasoactive substances. In some embodiments the other vasoactive substances are agonists of the alpha 1 adrenergic receptors. Alpha 1 adrenergic receptor agonists include methoxamine, midodrine, metaraminol, phenylephrine and amidephrine, with midodrine being a particularly preferred other vasoactive substance. In other embodiments, the other vasoactive substances include vasopressin (antidiuretic hormone) and vasopressin analogues. Vasopressin analogues include desmopressin and terlipressin. Other vasoactive substances can also include somatostatin analogs, such as octreotide.

In certain embodiments, patients treated in accordance with the invention will have a certain minimum level of kidney function. Kidney function is routinely assessed using creatinine—higher creatinine levels are indicative or reduced kidney function. Normal creatinine levels in the blood are typically between 0.5 and 1.2 milligrams per deciliter. In many cases a patient will have a serum creatinine level of <2 mg/dL. In other cases, a patient will have serum creatinine levels of <1.5 mg/dL. In still other cases a patient will have serum creatinine levels of <1 mg/dL.

It is contemplated that cirrhotic patients with ascites will have an altered renin-angiotensin-aldosterone system and, without being held to a particular mechanism of action, that docarpamine treatment of ascites will be more effective in patients with elevated renin and/or elevated aldosterone levels. Thus, some embodiments of the invention relate to treating patients having an aldosterone level exceeding 21 ng/dL (582.5 pmol/L) and/or a serum renin concentration exceeding 40 pg/mL (1.0 pmol/L).

The invention contemplates the treatment of refractory ascites patients who have low urinary sodium excretion even while on diuretic therapy. Normal ranges are 40-220 mEq/day (mmol/day) and patients treated according to the invention will typically have a total daily (i.e., 24 hour) sodium excretion of less than 40 mEq day. In some embodiments, sodium excretion in the presence of diuretics (e.g., spironolactone and furosemide) will be less than 30 mEq/day, less than 20 mEq/day, less than 10 mEq/day or even less than 5 mEq/day. Spot urine tests in such patients will yield sodium of less than 20 mEq/L and more generally less than 15 mEq/L, less than 10 mEq/L, less than 5 mEq/L or even less than 1 mEq/L, despite treatment with diuretics. In some cases spot urine sodium will be less than 0.1 mEq/L, less than 0.01 mEq/L or even undetectable. Spot urinary Na/K ratio will be less than 1 and sodium excretion in response to a single intravenous dose of 80 mg furosemide will be less than 50 mEq/8 hours.

The inventors have also observed that the oral administration of docarpamine results in a high degree of variability in the resulting dopamine levels in non-Asian (especially Caucasian) populations, as compared to Asian (especially Japanese) populations. Accordingly, titrating the dose in such highly variable populations is warranted. Thus, another embodiment relates to a method of treating a patient with ascites, comprising: administering to said patient a first amount of docarpamine; obtaining the concentration of dopamine in the blood, serum or plasma of said patient; and administering a second amount of docarpamine to said patient, wherein said second amount is selected based on the concentration of dopamine obtained. Typical target plasma levels for dopamine in this regard will be between 1 and 300 ng/ml. Preferable target plasma levels will be between 10 and 150 ng/ml with more preferred target plasma levels being from 20-110 ng/ml or 20-80 ng/ml. Most preferred target plasma levels are from 40-80 ng/ml.

Embodiments of the present disclosure can be further defined by reference to the following examples. It will be apparent to those skilled in the art that many modifications, both to materials and methods, can be practiced without departing from the scope of the present disclosure. As used herein and in the appended claims, the singular forms "a," "or," and "the" include plural referents unless the context clearly dictates otherwise.

Example 1: Clinical Study

Design

An open-label, single-arm study in which each subject serves as his/her own control is conducted. The study assesses the effect of DCP treatment on ascites formation in cirrhotic subjects with RA, by examining the frequency of LVP and the volume of ascitic fluid drained. All subjects participate in a 90-day open-label treatment period. One group receives 750 mg docarpamine 3 times per day (total daily dose of 2250 mg) and a second group receives 1500 mg docarpamine 3 times per day (total daily dose of 4500 mg), followed by a 90-day follow-up. Ascites history (relevant medications, LVP dates, and volume of drained fluid) for the 90 days prior to treatment and the 90 days after treatment are collected and used for comparison with on-treatment frequency and volume.

Study Population

The study population consists of cirrhotic patients between 18 and 70 years of age, inclusive, with refractory ascites, subject to the following inclusion and exclusion criteria.

Inclusion Criteria
Patients 18 years to 70 years of age.
Documented cirrhosis of the liver.
Refractory ascites, defined as ascites not manageable with diuretics and diet restriction, managed with periodic large volume therapeutic paracentesis.
Patients must have therapeutic paracenteses in the 3 days prior to enrollment and a documented minimum of 3 additional therapeutic paracenteses in the 90 days prior to enrollment, with at least 1 every 30 days.
Outpatient, with expected survival of at least 6 months.
Willing and able to complete an informed consent form.

Exclusion Criteria
Ascites due to any cause other than cirrhosis such as malignant ascites.
Existing or planned placement of Transjugular Intrahepatic Portosystemic Shunt or other surgical shunts.
Active bacterial infection.
Scheduled organ transplantation within the next 6 months.
Change in diuretics schedule within 60 days prior to initiation of treatment.
Model for End-stage Liver Disease-sodium Score of >25.
Serum creatinine >2 mg/dL.
Serum bilirubin >5 mg/dL.
International Normalized Ratio >1.5.
Hepatocellular Carcinoma Barcelona Classification of Liver Cancer stage C or above.
Current or recent (within 3 months of consent) renal dialysis.
Hepatic encephalopathy grade 3 or 4.
Pheochromocytoma or hypertrophic obstructive cardiomyopathy.
Current or recent treatment (within 7 days) with octreotide, midodrine, vasopressin, dopamine or other vasopressors.
Current or recent treatment (within 21 days) with monoamine oxidase inhibitors, tricyclic antidepressants, phenytoin, haloperidol or haloperidol-like drugs, or phenothiazines such as prochlorperazine.
Episode of spontaneous bacterial peritonitis or gastrointestinal hemorrhage, or any acute decompensation within 30 days of enrollment.
Severe cardiovascular disease such as congestive heart failure, advanced arteriosclerosis, coronary insufficiency, tachyarrhythmia, or uncontrolled hypertension above 160/100.
Known or suspected extra-hepatic malignancy (other than skin cancer and in-situ cancers), unless adequately treated.
Pregnant females, females anticipating pregnancy during study period, or breastfeeding.
Known allergy or hypersensitivity to dopamine or docarpamine.
Any severe comorbidity that in the opinion of the Investigator would disallow safe participation in the trial.
Participation in other clinical research studies involving the evaluation of other investigational drugs or devices within 90 days of consent.

Results

Following 90 days for treatment the following effects are observed, but only in the high dose (4500 mg per day group). Some patients do not require LVP for more than one month and others do not require LVP for more than two months. Overall, the frequency of LVP and/or the volume of ascites removed over 90 days was reduced by more than half on average. Increased sodium excretion and other markers of improved renal function respond positively. Most patient go from 500-1000 ml urinary output to 1500-2000 ml or more. Renin and/or aldosterone levels are reduced, in some cases to normal, in many patients. It is concluded that the optimal dose of docarpamine is 4500 mg per day.

In a study conducted in accordance with the foregoing, some patients treated with 2250 mg per day in combination with diuretics have showed an enhanced response (decreased need for LVP). One such patient was also administered furosemide 20 mg per day and spironolactone 300 mg per day. Other patients also administered furosemide 40 mg or 240 mg per day and spironolactone 100 mg per day. Finally, one patient was administered spironolactone 75 mg per day with docarpamine, but without any furosemide.

REFERENCES

Lin S M, Lee C S, Kao P F. Low-dose dopamine infusion in cirrhosis with refractory ascites. Int J Clin Pract. 1998 November-December; 52(8):533-6.

Hadengue A, Moreau R, Bacq Y, Gaudin C, Braillon A, Lebrec D. Selective dopamine DA1 stimulation with fenoldopam in cirrhotic patients with ascites: a systemic, splanchnic and renal hemodynamic study. Hepatology. 1991 January; 13(1):111-6.

Yannick Bacq Christophe Gaudin Antoine Hadengue Dominique Roulot Alain Braillon Richard Moreau Dr. Didier Lebrec. Systemic, splanchnic and renal hemodynamic effects of a dopaminergic dose of dopamine in patients with cirrhosis. Hepatology. 1991. 14(3): 483-487.

David E Barnardo, William P Baldus, Frank T Maher. Effects of Dopamine on Renal Function in Patients with Cirrhosis. Gastroenterology. 1970. 58(4): 524-531.

A Mostbeck, L Peschl, J Schüller, A Neumayr. The simultaneous investigation of liver and kidney function in the presence of dopamine. Wien Klin Wochenschr. 1975 Oct. 17; 87(19):639-42.

Carmelita R. Espiritu, Jose P. Mendoza, Billy K. Yeh. Effects of Intravenous Infusion of Dopamine in Cirrhotics. Proc Soc Exp Biol Med. 1972 October; 141(1):331-5.

Runyon B A, Montano A A, Akriviadis E A, et al. The serum-ascites albumin gradient is superior to the exudate-transudate concept in the differential diagnosis of ascites. Annals. of Internal Medicine. 1992; 117:215-220.

Salerno F, Guevara M, Bernardi M, et al. Refractory ascites: pathogenesis, definition and therapy of a severe complication in patients with cirrhosis. Liver Int. 2010; 30(7): 937-947.

Pose E, Cardenas A. Translating our current understanding of ascites management into new therapies for patients with cirrhosis and fluid retention. Dig. Dis. 2017; 35(4): 402-410.

P Ginés, E Quintero, V Arroyo, J Terés, M Bruguera, A Rimola, J Caballería, J Rodés, C Rozman. Compensated cirrhosis: natural history and prognostic factors. Hepatology. January-February 1987; 7(1): 122-8.

Piano S, Tonon M, Angeli P. Management of ascites and hepatorenal syndrome. Hepatol. Int. 2018; 12(Suppl 1):122-134.

La Mura V, Salerno F. Therapy of the refractory ascites: Total paracentesis vs. TIPS. Gastroenterol. Hepatol. 2016; 39(7):477-480.

Zhao R, Lu J, Shi Y, et al. Current management of refractory ascites in patients with cirrhosis. J. Int. Med. Res. 2018; 46(3):1138-1145.

Funasaki T, Tsutsumi M, Takase S, et al. Effects of a new orally active dopamine prodrug, docarpamine, on refractory ascites: A pilot study. Am. J. Gastroenterology. 1999; 94(9):2475-2481.

Caitlin Hodge M D, MPH Brian D. Badgwell M D, MS. Palliation of malignant ascites. Jul. 1, 2019. J Surg Oncol. 120(1): 67-73.

Egbert Frick Jiirgen Schölmerich. Etiology, Diagnosis, and Management of Non-Cirrhotic Ascites. Book Editor(s): Pere Ginès Vicente Arroyo Juan Rodés Robert Schrier. 12 Jul. 2005 https://doi.org/10.1002/9780470987476.ch24. ISBN: 9781405118040 (Wiley).

Fabiolla Siqueira, M D, Traci Kelly, N P, and Sammy Saab, M D, MPH, AGAF. Refractory Ascites: Pathogenesis, Clinical Impact, and Management. Gastroenterol Hepatol (NY). 2009 September; 5(9): 647-656.

V Arroyo, P Ginés, A L Gerbes, F J Dudley, P Gentilini, G Laffi, T B Reynolds, H Ring-Larsen, J Schölmerich. Definition and diagnostic criteria of refractory ascites and hepatorenal syndrome in cirrhosis. International Ascites Club. Hepatology. 1996 January; 23(1):164-76.

Kevin P Moore, Florence Wong, Pere Gines, Mauro Bernardi, Andreas Ochs, Francesco Salerno, Paolo Angeli, Michael Porayko, Richard Moreau, Guadelupe Garcia-Tsao, Wladimiro Jimenez, Ramon Planas, Vicente Arroyo. The management of ascites in cirrhosis: report on the consensus conference of the International Ascites Club. Hepatology. 2003 July; 38(1):258-66.

Bruce A. Runyon. Management of Adult Patients with Ascites Due to Cirrhosis: An Update. 2013. Hepatology, 49(6): 2009.

What is claimed is:

1. A method of treating a patient with ascites, comprising administering to said patient a therapeutically effective amount of docarpamine, wherein said therapeutically effective amount of docarpamine is greater than 2,250 mg per day.

2. The method according to claim 1, wherein said therapeutically effective amount of docarpamine is greater than 3,500 mg/day.

3. The method according to claim 1, wherein, prior to said administering docarpamine, the patient is treated for more than 1 week with doses of furosemide >80 mg/day and/or spironolactone >100 mg/day.

4. The method according to claim 3 wherein the patient does not exhibit diuretic-induced renal impairment.

5. The method according to claim 1, further comprising at least one second administration of docarpamine during which said patient is also being treated with furosemide >80 mg/day and/or spironolactone >100 mg/day.

6. The method according to claim 1, wherein said ascites is caused by liver cirrhosis due to alcohol or non-alcoholic fatty liver disease.

7. The method according to claim 1, wherein said ascites is not caused by cirrhosis due to viral hepatitis or primary biliary cholangitis.

8. The method according to claim 1, wherein said patient has a serum aldosterone level exceeding 21 ng/dL (582.5 pmol/L) and/or a serum renin concentration exceeding 40 pg/mL (1.0 pmol/L).

9. The method according to claim 1, wherein, prior to treatment, said patient required large volume paracentesis at a minimum of: (a) 3 times in 60 days, (b) 4 times in 90 days or (c) at least once every 30 days over a 90-day period.

10. The method according to claim 1, wherein said patient's ascites is unresponsive to intensive diuretic therapy.

11. The method according to claim 1, wherein prior to treatment said patient has a 24-hour urinary sodium excretion of less than 40 mEq during treatment with one or more diuretic agents.

12. The method according to claim 1, wherein said patient has diuretic intractable ascites, and the patient experienced one or more diuretic-induced complications selected from the group consisting of: diuretic-induced hepatic encephalopathy; diuretic-induced renal impairment; diuretic-induced hyponatremia; and diuretic-induced hypokalemia.

* * * * *